United States Patent [19]

Svendsen

[11] Patent Number: 5,463,466
[45] Date of Patent: Oct. 31, 1995

[54] APPARATUS FOR ANALYZING OPTICAL PROPERTIES OF TRANSPARENT OBJECTS

[75] Inventor: David A. Svendsen, St. Giles Hill, United Kingdom

[73] Assignee: York Technology Limited, Hants, United Kingdom

[21] Appl. No.: 392,299

[22] Filed: Feb. 22, 1995

Related U.S. Application Data

[63] Continuation of Ser. No. 940,908, filed as PCT/GB91/00716, May 3, 1991, abandoned.

[30] Foreign Application Priority Data

Apr. 4, 1990 [GB] United Kingdom ............... 9010181

[51] Int. Cl.$^6$ ............................................. G01N 21/47
[52] U.S. Cl. .......................... 356/440; 356/128; 356/73.1
[58] Field of Search ............................ 356/440, 432, 356/244, 246, 73.1, 128, 129, 133; 250/576

[56] References Cited

U.S. PATENT DOCUMENTS

| | | | |
|---|---|---|---|
| 3,529,896 | 9/1970 | Padawer | 356/246 |
| 4,208,126 | 6/1980 | Cheo et al. | 356/73.1 |
| 4,227,806 | 10/1980 | Watkins | 356/73.1 |
| 4,441,811 | 4/1984 | Melezoglu et al. | 356/128 |
| 4,515,475 | 5/1985 | Payne et al. | 356/73.1 |
| 4,799,787 | 1/1989 | Mason | 356/44 |

FOREIGN PATENT DOCUMENTS 61-266932  11/1986  Japan.
2071315   3/1981   United Kingdom.

OTHER PUBLICATIONS

Applied Optics, vol. 18, No. 13, 1 Jul. 1979, L. S. Watkins: "Laser beam refraction traversely through a graded-index preform to determine refractive index ration and gradient profile", pp. 2214–2222.

Applied Optics, vol. 189, No. 1, Jan. 1979, D. Marcuse et al.: "Focusing method for non-destructive measurement of optical fiber index profiles," pp. 14–22.

*Primary Examiner*—Hoa Q. Pham
*Attorney, Agent, or Firm*—Dressler, Goldsmith, Shore & Milnamow, Ltd.

[57] ABSTRACT

Apparatus for analysing the optical properties of a transparent object (118) comprises a light source, an analyser cell comprising a body of solid transparent material (110) having a cavity (112) formed therein for receiving the object (118) to be analysed, and arranged so as to allow a light beam from the light source to pass through the object (118), said body (110) having an entrance surface (114) through which the light beam enters the cell from the ambient medium and an exit surface (116) through which the light beam leaves the cell, and analysing means for analysing the light beam after passage through the object (118), and is characterised in that the cavity (112) in the analyser cell is of substantially circular section in at least the region through which the light beam passes in use.

11 Claims, 3 Drawing Sheets

APPARATUS FOR ANALYZING OPTICAL PROPERTIES OF TRANSPARENT OBJECTS

This is a continuation, of application Ser. No. 07/940,908, filed as PCT/GB91/00716, May 3, 1991 now abandoned.

FIELD OF THE INVENTION

This invention relates to an apparatus and method for analysing the optical properties of a selected cross-section of a transparent object, and to an analyser cell for use in such apparatus and method.

DESCRIPTION OF RELATED ART

A knowledge of the refractive index profile of an object such as an optical fibre preform is important for ensuring the quality control of its manufacture. One known type of apparatus for measuring and analysing this refractive index profile is described by L. S. Watkins in Applied Optics, 1st July 1979, Vol. 18, No. 13, pp. 2214 to 2222, and I. Sasaki et al. in Electronics Letters, 13th March 1980, Vol. 16, No. 6, pp. 219 to 221. Such an apparatus (known as a "preform analyser") utilises transverse illumination of the preform and detection of certain of the properties of the illuminating beam once it has passed through the preform. One recent version of preform analyser is disclosed in International Patent Application No. PCT/GB89/01352.

In order to obtain results of useful quality using a preform analyser, it is known, for example from United Kingdom Patent Application No. GB-A-2071315, to immerse a section of the length of the preform in a liquid (known as "index matching liquid") which has a refractive index approximately matching that of the preform. As further disclosed in this document, this liquid is contained in what is generally termed an analyser cell, which takes the form of a transparent container of rectangular cross-section. The preform extends through two opposing side walls of the container, a seal being effected by two "O" rings. The other two opposing side walls are glass windows through which the illuminating beam is shone. Often, liquid pumping and flow apparatus is used to empty and fill the container, especially when the liquid is toxic.

Japanese Patent Application No. JP 61-266932 discloses an analyser cell assembly generally similar to that described above, but incorporating a circularly cylindrical transparent sheath of known refractive index interposed concentrically with the preform between the preform and the container. The sheath acts as a reference from which the absolute value of the refractive index profile of the preform can be deduced.

It has been found that, whilst index matching liquid enables useful refractive index measurements to be made, known analyser cells suffer from various disadvantages. Firstly, significant problems have been encountered due to the fact that index matching liquid generally has a refractive index which varies substantially with temperature. Typical liquid has a refractive index temperature coefficient of about −0.0004 per degree Celsius, which compares unfavourably with a typical required measurement precision equivalent to less than 0.00005 in refractive index difference. Thus temperature changes of as little as 0.1° C. in the liquid during the course of measurements can affect accuracy and lead to poorer repeatability than would be achieved if the liquid were at a constant temperature. Such small temperature changes are very difficult to avoid in most laboratories and manufacturing environments.

The above problems are exacerbated if, as is frequently desirable, the properties of the preform are measured soon after manufacture, since the preform may take a significant time to cool down from its molten state. In these circumstances, the temperature of the preform may change very significantly during the course of the measurements, and this may well in turn significantly affect the temperature of the index matching liquid and thus its refractive index.

Furthermore, it has now been discovered that even spatial variations in temperature within the liquid (leading to spatial variations in its refractive index) can lead to a distortion of the measured refractive index profile of the preform which is often of sufficient magnitude to negate the usefulness of the measurements. Such variations may arise when the preform is at a different temperature from the liquid or when the liquid is being heated by another source, such as the measurement apparatus itself. These spatial variations in temperature can also give rise to convection currents within the liquid which can cause unwanted temporal instability in the temperature profile of the liquid.

A second disadvantage of the known analyser cells is that the pumping equipment which they often employ may introduce air bubbles or solid contaminants into the liquid, which can degrade the quality of the measurements by causing light scattering and undesirable deviation of the illuminating beam.

SUMMARY OF THE INVENTION

According to the present invention, there is provided apparatus for analysing the optical properties of a transparent object, comprising a light source, an analyser cell comprising a body of solid transparent material having a cavity formed therein for receiving the object to be analysed, and arranged so as to allow a light beam from the light source to pass through the object, said body having an entrance surface through which the light beam enters the cell from the ambient medium and an exit surface through which the light beam leaves the cell, and analysing means for analysing the light beam after passage through the object, characterised in that the cavity in the analyser cell is of substantially circular section in at least the region through which the light beam passes in use.

The apparatus of the invention will usually be used for analysing the optical properties of objects having a generally circular section, and the annular space between the outer surface of the object and the internal surface of the cavity in the cell will be filled with index matching fluid. The present invention solves the problem identified earlier which arises when index matching fluid which has a substantial temperature coefficient of refractive index is utilised.

In the case of an object having a generally circular section, by constraining the fluid in an annular shape whose outer boundary is substantially geometrically similar to the shape of the object in the region which is being measured (i.e. by constraining the fluid in a circular annulus), if the fluid has either a substantially uniform refractive index or only a radial variation in refractive index (caused, for example, by the object being uniformly hotter than ambient), then it is indistinguishable, in a measurement and mathematical sense, from any circular annulus of the object itself. Thus the effect of any bulk change in the refractive index of the fluid during the investigations can be greatly reduced, for example by computational adjustments to measured results.

Similarly, appropriate adjustments can be made to measured results to correct for the presence of radial variations in the refractive index of the fluid.

Further, the constraint of the substantially circular section cavity assists in achieving a circularly symmetric thermal environment within the measurement region and in minimising the time taken for such circular symmetry to be achieved, so that the effects of circumferential variations in refractive index, for which adjustments cannot easily be made, can be minimised.

Even when the object does not have a generally circular section, the invention is still advantageous since, especially in the layers of fluid near the circular boundary of the cavity, that boundary tends to impress circular thermal symmetry on the fluid, regardless of the shape of the object. As described above, the effects of certain changes in the refractive index of the fluid can be corrected for in the regions of circular thermal symmetry.

A further advantage of the present invention is that, if the refractive index of the material of the analyser cell is known, it can be used as a stable refractive index reference point for the measurement of absolute refractive indices. The circular cavity is a particularly easy shape to reference to. The above advantage holds good whether or not the cross section of the object is generally circular.

The index matching fluid may be either a liquid or a gas. Preferably, although not necessarily, it has a refractive index at least approximately the same as that of the material of the analyser cell and/or the object; this maximises the effective observable region of the object and reduces the requirements on the quality of the surface finish of the object. One particularly useful and commercially available liquid is an aliphatic and alicyclic hydrocarbon mixture.

Generally, the ambient medium is air.

The object is typically an optical fibre or an optical fibre preform, although it could alternatively be, for instance, a gradient index rod lens or a sphere or other lens. It is preferred that the object is substantially completely solid, but it may, for example, comprise a solid element immersed in index matching fluid contained within a transparent container. Its outer boundary may typically be cylindrical, or at least quasi-cylindrical (in the sense of being, for example, tapered). As previously mentioned, the object is preferably of symmetrical section, at least in the region which is to be analysed, and more preferably elliptical and even more preferably circular, since this simplifies investigation of the optical properties of said cross-section. For preforms, circular (or quasi-circular) cross-sectional shapes are perhaps the most usual. There is no restriction on the diameter of the object apart from the appropriateness of the measurement apparatus and convenience.

The entrance and exit surfaces of the analyser cell are most conveniently flat, parallel and normal to the plane of the section of the object which is to be analysed, but are in any case preferably of a shape and quality that are matched to the analyser so that these interfaces have a minimal effect on the quality of the measurements.

The body of the analyser cell is preferably made of any material which has a neglible temperature coefficient of refractive index (e.g. glass) and preferably has a refractive index approximately matching the average index of the object, and more preferably approximately matching the index of the outer boundary of the object.

The entrance and exit surfaces need only be of general optical smoothness, and the material of the body of the cell itself of average homogeneity, since aberrations may be removed by characterising the measurement behaviour without the object and then subtracting the result when measuring with the object present. In preference, for convenience the entrance and exit surfaces and the homogeneity of the material of the body of the cell are of a quality easily achievable by usual workshop practices.

The analyser cell may have just one cavity or a plurality of cavities.

In preference, the analyser cell is in the form of a rectangular plate. Again in preference, the cavity is cylindrical with its longitudinal axis perpendicular to the plane of the plate, although this is by no means essential since correction may be made in the measured data. The plate is suitably of sufficient thickness to accommodate all angular deviations of the light beam out of the plane of the plate as occur, for instance, during the measurement of certain types of preforms, as taught in International Patent Application No. PCT/GB89/01352. It is preferably as thin as possible, typically 6 mm, for reasons of cost and convenience.

It is preferred that the maximum gap between the outer surface of the object, and the internal surface of the cavity in the cell is substantially less than the diameter of the object in that region, say, less than ¼, 1/10 or even 1/100 of the diameter of the object.

Providing for a relatively thin layer of fluid, especially in the region of the object which is to be analysed, affords considerable advantages over the known cells. Firstly, the problems of contamination, air bubbling, toxicity and cost of the fluid are significantly reduced because of the reduced volume of fluid used. The reduced volume of fluid used in turn allows the problems of contamination and air bubbling to be further ameliorated because it becomes feasible and possibly economic to use fresh fluid for each investigation or set of investigations, and pumping and flow apparatus can thus be dispensed with.

A second associated advantage is that because the need for pumping and flow apparatus can be eliminated, the cell can be made readily removable from the analyser. This allows the employment of a plurality of cells, each optimised for a particular use, and thus greatly extends the capability and versatility of the analyser. For example, different sizes or different refractive indices of analyser cell can be utilised. In addition, it would be possible to insert an object and fill the cell separately from the analyser, which allows longer times for thermal equilibrium to be achieved without preventing the analyser being used for other purposes. This is particularly useful in an optical fibre preform manufacturing environment when the time taken to measure preforms is often critical, and there is barely time to allow the preforms to cool fully to ambient temperatures.

Thirdly, by having a relatively thin layer of fluid, the rate at which thermal and thus refractive index homogeneity in the fluid can be achieved is substantially increased over that achievable with known cells.

It is thus advantageous that the volume of solid material in the cell, excluding the volume occupied by the object, is greater (preferably much greater) than the volume reserved for receiving the fluid. As compared with known cells, replacing the maximum possible volume of fluid by a solid material is particularly advantageous if the solid material has a negligible temperature coefficient of refractive index.

In a first particularly preferred embodiment of the invention, the index matching fluid is retained by surface tension, without any additional physical support. This allows a simple construction for the cell to be adopted. Dependent upon the size of the object and the nature of the fluid, this will usually mean that the annulus of index matching fluid is very thin, which enables the advantages of a small volume of fluid mentioned above to be realised.

Alternatively, the cell may be provided with fluid retaining means. These may comprise at least one seal fitted on the cell or the object or both, which seal is advantageously repellant to the fluid.

In a second particularly preferred embodiment, the retaining means comprises a seal around the object on one side of the cross-section which is to be analysed (which is particularly useful when said cross-section is substantially horizontal, so that the fluid can also be retained by gravity), and possibly also a further seal around the object on the other side of said cross-section.

By not relying on surface tension effects to retain the fluid, but instead providing a separate and independent retaining means, objects of different sizes can be held within the cell, particularly if the or each seal is flexible (made of rubber, for example) or differently sized seals are provided.

Preferably, the cell is provided with a thermally conductive ring member (typically made of metal) in the cavity, capable of thermal communication with the fluid. This enables thermal homogeneity in the fluid to be more quickly achieved, and also renders the thermal environment more stable by serving to reduce the rate of change of temperature within the fluid, which can be advantageous since it can improve the quality of measurements.

This facility for reducing temperature variations is especially advantageous when the object has a large thermal mass, when there are large temperature differences between the cell and the object, or when the annulus of index matching fluid is relatively large, since in these circumstances the temperature variations in the fluid may, even when the annulus has inner and outer boundaries geometrically similar to the shape of the object, be sufficiently large to cause errors.

The corollary of this is that, when the thermally conductive member is provided, larger amounts of fluid may be utilised for a given degree of measurement accuracy. This permits differently sized objects to be employed with the same cell, or at least with some of the same components of the cell. This is cheaper and simpler than, say, providing a plurality of analyser cells having differently sized cavities corresponding to differently sized objects.

The conductive member is preferably in thermal communication with the material of the analyser cell. This tends to create a yet more stable and isothermal environment.

The cell preferably includes thermal insulating means for reducing heat transfer between the cell and the environment whilst permitting heat transfer within said cell; this helps to create a uniform thermal environment within the cell and the fluid. The insulating means may be in the form of at least one thermally insulating ring member substantially completely enclosing the thermally conductive member, and preferably in contact therewith. It is thus preferable if the inner boundary of the thermally insulating member is substantially geometrically similar to shape of the object. Its outer boundary may be of any convenient form since this boundary is deemed to be at ambient temperature by virtue of its thermal insulating properties.

Preferably, the cell further comprises an orifice (suitably in the form of a filling hole) communicating with the cavity, whereby the cell can be filled with fluid. More preferably, it further comprises a second orifice communicating with the cavity, whereby air can be bled from the cell during filling. Alternatively, filling and emptying can be effected by other means, especially if surface tension is utilised to retain the fluid, or if the free surface of the fluid is exposed to the atmosphere, as might be the case if the cross-section to be analysed is substantially horizontal.

According to a further aspect of the present invention, there is provided an analyser cell for use in apparatus for analysing the optical properties of an optical fibre or optical fibre preform, said cell comprising a body of solid transparent material having a cavity formed therein for receiving the object to be analysed, said body having a substantially planar entrance surface for a light beam to enter the cell and a substantially planar exit surface for the light beam to leave the cell after passage through the object, characterised in that the cavity is substantially circular cylindrical.

Further provided by the present invention is a method of analysing the optical properties of a transparent object, comprising placing the object within the cavity of the analyser cell of the invention, placing index matching fluid in the gap between the outer surface of the object and the internal surface of the cavity, in at least the region of the object to be analysed, passing a light beam through the object, and analysing the light beam after passage through the object.

The present invention also provides a method of determining the temperature coefficient of refractive index of a fluid using the apparatus according to the present invention, including the steps of:

filling the cell with the fluid;

creating a known temperature gradient in the fluid between known points in a given plane;

analysing the refractive index profile of the fluid in said plane; and determining the temperature coefficient of refractive index of the fluid from the analysed refractive index profile and known temperature gradient.

The method may further include the step of placing a substantially circularly cylindrical object in the cavity in the cell. The object may conveniently be used as a heat source to create the temperature gradient, and, although it does not have to be transparent, it is conveniently an optical fibre or optical fibre preform. For results of high accuracy, the object is preferably transparent and of known refractive index.

Specific embodiments of the invention are now described, by way of example, with reference to the accompanying drawings, in which:

BRIEF DESCRIPTION OF THE DRAWINGS

In the drawings, like parts of the first or second embodiment are identified by the same reference numerals in the various figures.

DESCRIPTION OF THE PREFERRED EMBODIMENT

Figure 1:
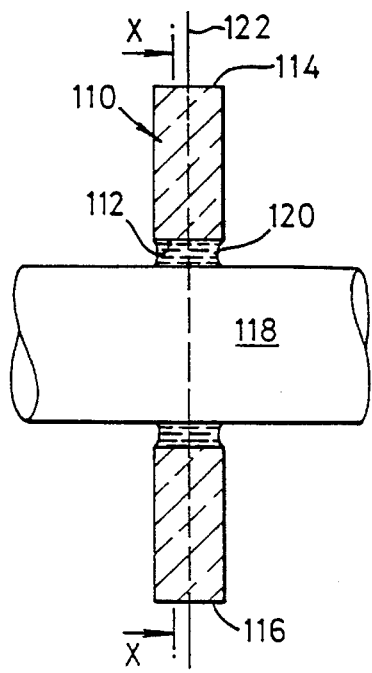
FIG. 1 is a part-sectional side elevational view of a first embodiment of analyser cell showing a preform in position.
Figure 2:
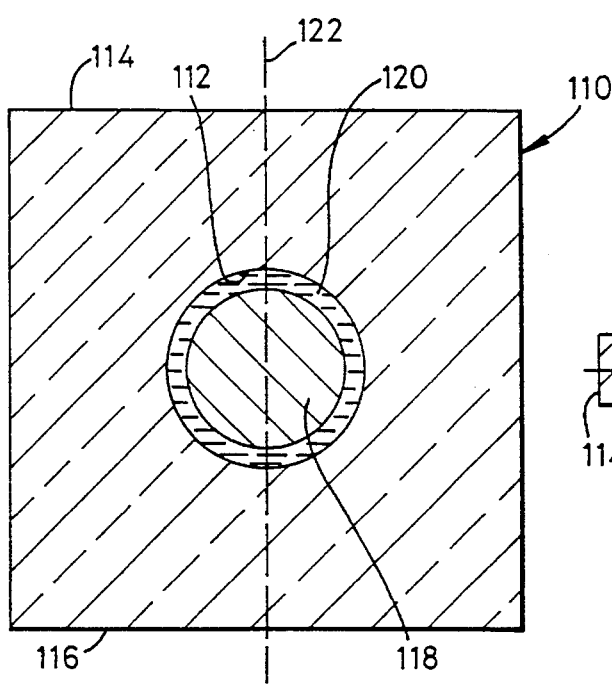
FIG. 2 is a cross-sectional view of the first embodiment, the section being taken on the line XX' of FIG. 1.

Referring to FIGS. 1 and 2, a first embodiment of analyser cell according to the present invention comprises an optically homogeneous, rectangular glass plate 110 having a central circular cavity 112 and entrance and exit surfaces 114 and 116 for illumination by a preform analyser of the type described above. The cavity 112 is defined by a surface as nearly cylindrical and perpendicular to the surface of the plate 110, and as nearly optically smooth, as is achievable by usual optical workshop practices. Again, the entrance and exit surfaces 114 and 116 are as nearly optically flat, parallel to each other and perpendicular to the surface of the plate 110 as is achievable by the usual workshop practices.

In use, the cell is inserted over a circularly cylindrical optical fibre preform 118, as shown in FIGS. 1 and 2, and held firmly and centrally in place by retaining means (not shown). The annulus between the cell and the preform 118 is filled using a hypodermic syringe and needle with liquid 120 having an index approximately matching that of the preform 118 and plate 110. The cavity 112 is so dimensioned with respect to the preform 118 that the liquid 120 in the annulus is sufficiently thin for surface tension to hold it in place. Measurement of the optical properties of the preform 118 is carried out by illuminating, using a preform analyser, the cell and preform with a beam parallel to a measurement optical axis 122, in accordance with techniques well known to the skilled person and described earlier.

For a given size of preform 118 the plate 110 is for cost and convenience as thin as possible commensurate with the requirement that it accommodates all angular deviations in the direction of the longitudinal axis of the preform. For instance, for a preform of 5 mm diameter, the plate might typically be 3 mm thick. The annulus of liquid 120 is typically very thin, so that a minimal quantity of the liquid is required.

It will be appreciated that the plate 110 could be placed in an unmodified conventional analyser cell of the type described, for example, in United Kingdom Patent Application No. 2071315. Alternatively, the plate 110 could replace the cell windows of such a conventional cell, with the cell otherwise unmodified.

Figure 3:
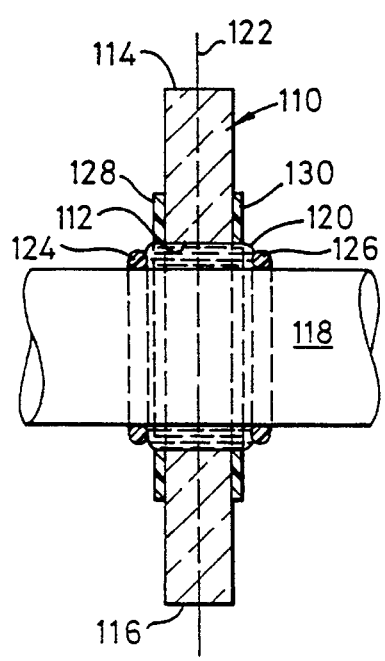
FIG. 3 is a view similar to that of FIG. 1 showing a first alternative arrangement for retaining index matching liquid.

As shown in FIG. 3, a first alternative arrangement for retaining the liquid 120 utilises the same basic cell as that described with reference to FIGS. 1 and 2. Surface tension effects are still utilised to retain the liquid. However, in addition, the cell further comprises two collars 124 and 126, and two disc-shaped surface coatings 128 and 130 applied to the faces of the plate 110. The collars 124 and 126 and coatings 128 and 130 are made so that they are repellant to the liquid, that is, they are not "wetted" by it. Under these conditions, the liquid is retained, air bubbles do not form and the liquid very rapidly reaches a thermal equilibrium of the desired circularly cylindrical symmetry. With this arrangement, the axis of the preform 118 can be placed at any convenient angle to the vertical without the liquid 120 being lost.

The skilled person can determine by simple experiments which materials are not wetted by a particular index matching liquid. As an example, if water is used as the index matching liquid, the collars can be rendered repellant to it by being covered with a coating of grease.

Figure 4:
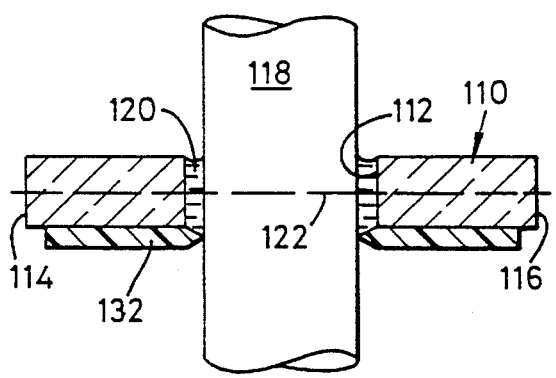
FIG. 4 is a view similar to that of FIG. 1 showing a second alternative arrangement for retaining the index matching liquid, the preform being shown in a vertical attitude.

It will be appreciated that the arrangements for retaining the liquid 120 shown in FIGS. 1 to 3 are most appropriate for preforms (or other similar objects such as optical fibres) of relatively small diameter, say 0.1 mm to 5 mm. A second alternative arrangement for retaining the liquid 120 is now described with reference to FIG. 4. This arrangement is suitable for use with a wider range of preform diameters or with materials whose properties do not easily retain the liquid.

Again, the same basic cell as that described with reference to FIGS. 1 and 2 is utilised. The cell is provided, in addition to the features of the cell described with reference to FIGS. 1 and 2, with a flexible annular seal 132 bonded or otherwise attached to the under surface of the plate 110, and is held in a vertical or near vertical attitude (in other words, with the longitudinal axis of the preform 118 vertical). The liquid 120 is introduced from above under the pull of gravity. With the cell held in a vertical or near vertical attitude it will be understood that any air bubbles introduced into the liquid rapidly gravitate away from the measurement optical axis 122.

A second embodiment of analyser cell according to the present invention is now described with reference to FIGS. 5 and 6. The cell includes a glass plate 210 which is substantially the same as that of the first embodiment, except that it is not necessarily arranged in combination with the preform so as to form a thin annulus therebetween. Thus the plate possesses a circular cavity 212, entrance surface 214 and exit surface 216 just as in the first embodiment. Again, the cell is used in combination with an optical fibre preform 218 and liquid 220, and has the same measurement optical axis 222 as described previously.

However, the second embodiment of cell further comprises two thermally conductive, circularly cylindrical rings 224 and 226, each manufactured from aluminium and each attached to respective ones of the sides of the plate 210. Each ring 224,226 has corrugations (not shown) on its faces which are in contact with the liquid 220 during use, to aid heat transfer. It will be understood that the corrugations are optional features.

Figure 5:
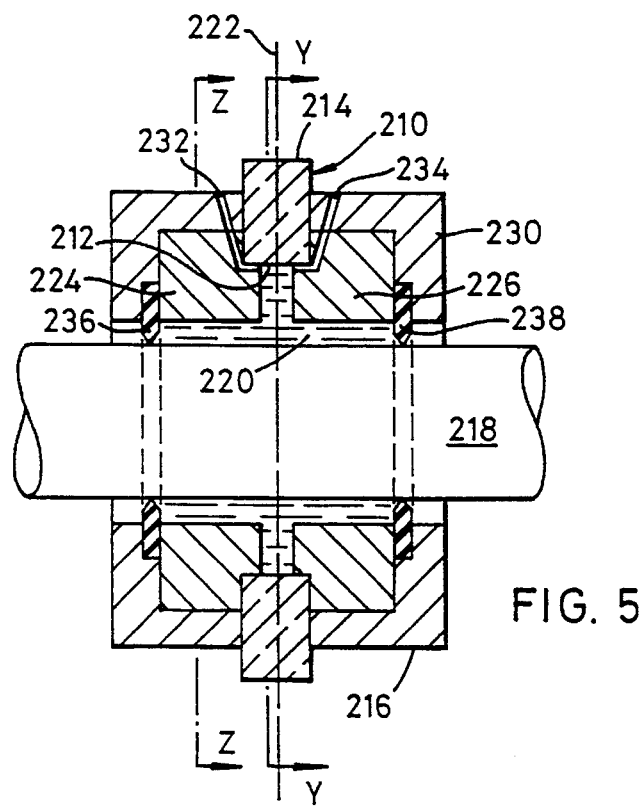
FIG. 5 is a part-sectional side elevational view of a second embodiment of analyser cell showing the preform in position.
Figure 6A:
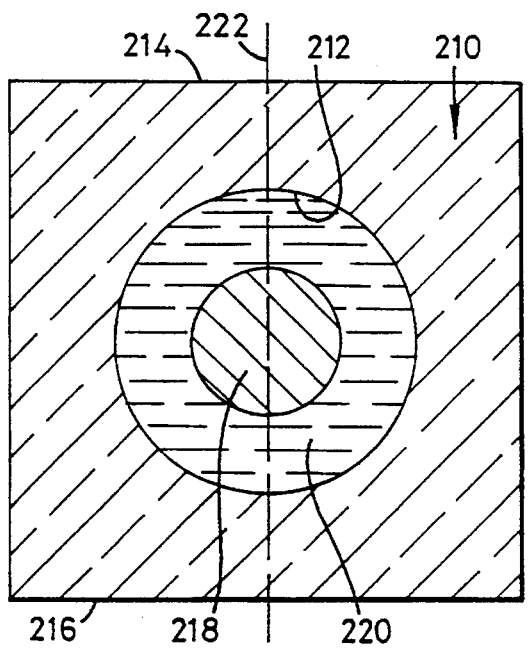
FIGS. 6a and 6b are cross-sectional views of the second embodiment, the sections being taken on the lines YY' and ZZ' respectively of FIG. 5.
Figure 6B:
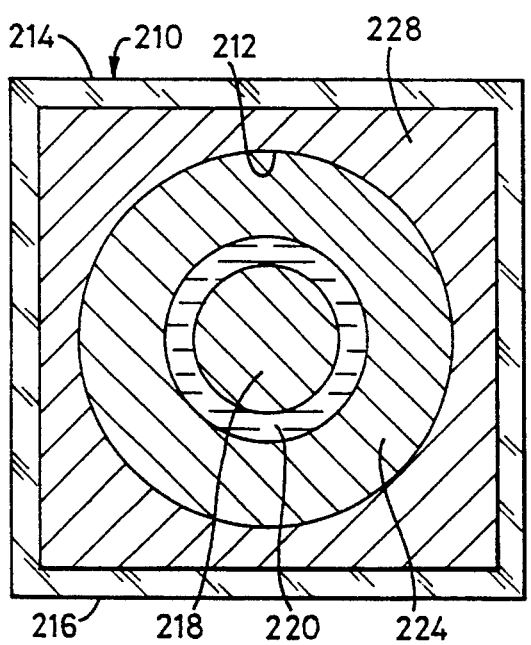

Two matching, thermally insulating, outer members 228 and 230, shaped as shown in FIGS. 5 and 6, are attached to the plate 210 by four bolts (not shown), one running through one each of the four corners of member 228, plate 210 and member 230, retained by nuts. The members 228 and 230 are a close fit with their respective rings 224 and 226. Small filling holes 232 and 234 in the respective rings 224 and 226 and outer members 228 and 230 are formed in the top face of the cell so that filling of the liquid 220 is gravity assisted. Flexible rubber ring seals 236 and 238 for retaining the liquid 220 during use are attached to outer members 228 and 230 respectively and project inwardly therefrom.

In use, the cell is inserted over the preform 218 and is held firmly in place thereon by the ring seals 236 and 238 and by suitable additional retaining means (not shown) as appropriate to the size and weight of the preform. When assembled, the rings 224 and 226 substantially fill the annular region between the plate 210 and the preform 218 in such a way as to minimise the volume of the region without obscuring the optical path through the plate 210. The whole region between the cell and the preform is filled with the liquid 220 via the filling holes 232 and 234 using one of three methods. Firstly, the liquid 220 may be injected through one of the filling holes 232 or 234 using a hypodermic syringe and needle. Air bubbles are prevented from forming in the liquid by the other of the filling holes 232 or 234 acting as an air bleed. The liquids removed by absorbent paper tissue or the like when the cell is removed after measurement has taken place, so that only fresh liquid is used and there is a consequently reduced chance of the liquid becoming contaminated by particles or air bubbles. Secondly, a small reservoir of liquid may be connected to one of the holes 232 or 234. As a third alternative, both holes 232 and 234 may be connected to a pumping and reservoir system so that the process of filling and emptying is achieved fully automatically, as in known preform handling techniques. It will be appreciated that with this last technique fresh liquid is not necessarily used for each separate measurement (or sets of measurements).

During use the thermally conductive, circularly cylindrical rings 224 and 226 act as a thermal boundary which impresses thermal circularly cylindrical symmetry on that portion of the liquid 220 in the measurement region (that is, that portion of the liquid adjacent the measurement optical axis 222). The remainder of the liquid fulfils the important function of thermally interfacing the preform to the rings 224 and 226 and thus provides a thermal boundary path which accelerates the flow of heat between the preform 218 and the cell when there is a temperature differential between them. The thermally insulating outer members 228 and 230 also assist in attaining thermal circularly cylindrical symmetry of the liquid 220 in the measurement region by restricting flow of heat out of the rings 224 and 226 and thus encouraging flow of heat into the glass plate 210.

It will be appreciated that, in the second embodiment, a single glass plate 210 may be provided for accommodating preforms having a range of different diameters. It would normally be necessary to provide different rings 224 and 226, outer members 228 and 230 and ring seals 236 and 238 appropriate to each different preform. It will be understood that the glass plate 210 is usually the most expensive item in the cell.

It will also be appreciated that the second embodiment of cell may take any required position relative to the vertical. The orientation of the cell is of consequence as concerns the ease with which it can be filled and with which air bubbles can be removed. If the cell is orientated so that the preform is substantially vertical, it will be understood that half of the components (for example, ring 226, outer member 230 and ring seal 238, together with filling hole 234) can be dispensed with. This facilitates filling of the cell and still provides an approximately cylindrically symmetric thermal environment for the liquid 220. However, this will not generally achieve the same quality of performance as is obtainable if all the above components are present.

Figure 7:
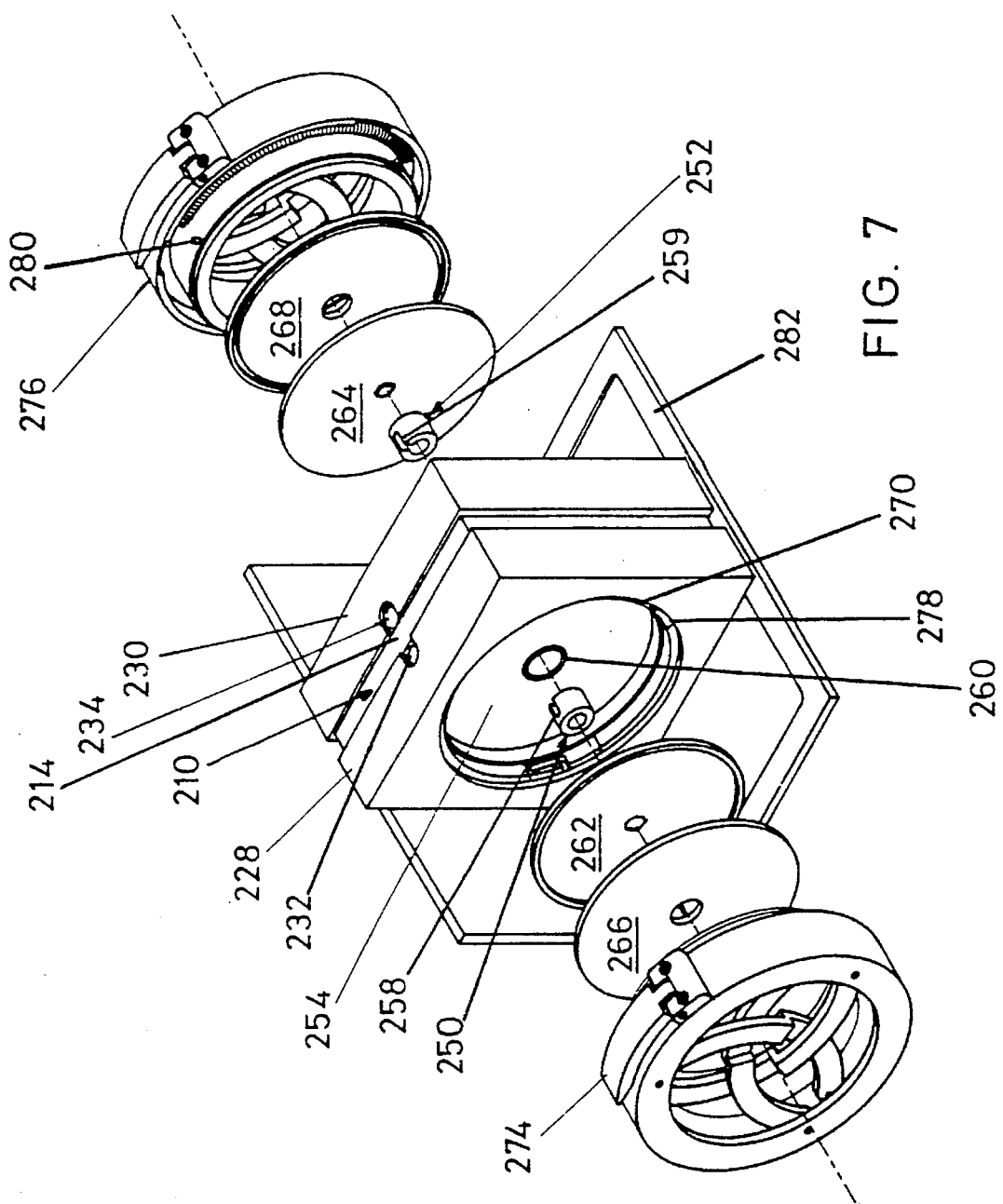
FIG. 7 is an exploded view of a modified version of the second embodiment.

In a modified version of the second embodiment of analyser cell illustrated in FIG. 7, the glass plate 210, outer members 228 and 230 and filling holes 232 and 234 are the same as in that version of the second embodiment shown in FIGS. 5 and 6, except that the glass plate is somewhat smaller (although this is of no material significance). However, the thermally conductive rings 224 and 226 are each provided as two distinct parts, inner rings 250 and 252 and respective outer rings 254 and 256 (outer ring 256 not being visible), the inner rings being friction fits in their respective outer rings. In fact, a plurality of interchangeable inner rings 250 and 252 would normally be provided having different inner diameters to fit preforms of different diameters. This allows the cell to be reconfigured quickly for use with different preforms.

Each inner ring 250 and 252 has a respective slot 258,259 to assist in clearing air bubbles from the index matching liquid 220. Each outer ring 254 and 256 has a respective raised sealing edge 260, 261 (edge 261 not being visible) which assists in providing a good seal between the outer ring and its respective seal 262,264.

Instead of ring seals 236 and 238, disc seals 262 and 264 together with their respective seal holders 266 and 268 are provided. Each seal holder is rimmed for retaining its disc seal, and is a sliding fit in the central aperture 270,272 (aperture 272 not being visible) in its respective outer member 228,230.

Means for supporting and retaining the preform is provided in the form of two chuck assemblies 274 and 276 which are attached to their respective outer members 228 and 230 by bayonet arrangements 278 and 280 (only a part of each of which is visible). The chuck assemblies are of the iris type well-known to the skilled person. The chuck assemblies 274 and 276 also retain the seal holders 266 and 268 and their respective seals 262 and 264 in place and exert a slight pressure on the seal holders to ensure a liquid tight seal between the disc seals and the raised sealing edges 260 and 261 on the outer rings 254 and 256.

The cell includes a fixing bracket 282 although any other suitable type of attachment may be used.

The cell described above could be used for determining the temperature coefficient of refractive index of the index matching liquid in conjunction with the preform analyser also described above. The preform could be replaced with a metallic or glass tube, and a source of heat, such as a heating element or a flow of heated liquid, placed in the centre of this tube. By measuring the temperature of the glass plate (110 or 210) and the temperature of the heat source, the thermal gradient across the liquid (120 or 220) in the measurement region will be known. A measurement of the refractive index of the liquid with respect to the glass plate using the preform analyser permits the refractive index gradient to be matched to the temperature gradient, hence revealing details of the temperature coefficient of the liquid.

It will be appreciated that the glass plate 110 or 210, instead of having a single aperture 112 or 212, could have a number of apertures either of different diameters or each having the same diameter. This would allow more than one preform (or other appropriate object) to be analysed in the same scan. For example, a plurality of apertures having a graded range of diameters could be provided in a rectangular plate, and could be used in the measurement of, for instance, 1 to 5 mm diameter SELFOC (trade mark) graded index rod lenses.

It will of course be understood that the present invention has been described purely by way of example, and modifications of detail can be made within the scope of the invention.

I claim:

1. Apparatus for analysing the optical properties of a transparent object, comprising a light source, an analyser cell which includes a body of solid transparent material having a cavity formed therein for receiving the object to be analysed, and arranged so as to allow a light beam from the light source to pass through the object, the body having an entrance surface through which the light beam enters the cell from an ambient medium and an exit surface through which the light beam leaves the cell, and analysing means for analysing the light beam after passage through the object wherein the cavity in the analyser cell is of a substantially circular section in at least a first region through which the light beam passes in use, wherein at least one heat conductive ring member is provided in a second region within said cavity and wherein the ring member defines a central opening for receiving the object and substantially fills the second region except for the central opening.

2. Apparatus according to claim 1 wherein the entrance and exit surfaces are substantially planar.

3. Apparatus according to claim 1, wherein the cell is provided with one or more fluid retaining seals.

4. An analyser cell for use in an apparatus for analysing the optical properties of an optical fibre or optical fibre preform, said cell comprising a body of solid transparent material having a substantially circular, cylindrical cavity formed therein for receiving the object to be analysed, said body having a substantially planar entrance surface for a light beam to enter the cell and a substantially planar exit surface for the light beam to leave the cell after passage through the object, wherein at least one heat conductive ring member is provided within said cavity and wherein the member defines a central opening for receiving the object and substantially fills the region except for the central opening.

5. An apparatus for analysing an optical property of an object having an axially extending dimension with a predefined cross-section oriented substantially perpendicular to the axially extending dimension, wherein that entire cross-section is substantially transparent such that a beam of radiant energy can be directed along said cross-section through at least a central region of the object, the apparatus comprising:

a housing which defines a bounded interior region with entry and exit ports for receiving the object with the axially extending dimension thereof extending through said interior region, between said ports;

a substantially planar, solid, transparent element with an opening which extends therethrough wherein said element is carried by said housing and extends into said interior region with said ports aligned with said opening;

at least one heat conductive member with an object receiving aperture which extends therethrough, wherein said conductive member is positioned adjacent to said element and wherein said aperture, said ports and said opening of said element are aligned such that said element and said member fill said interior region of said housing except for an object receiving region bounded, at least in part, by said opening and said aperture wherein when said housing receives the object to be analysed, the axially extending dimension thereof extends through, said object receiving region and the object substantially fills same and wherein the beam of radiant energy can be directed along the cross-section and through the central region of the object.

6. An apparatus as in claim 5 which includes a second heat conductive member with a second object receiving aperture which extends therethrough wherein said conductive members are spaced apart from one another by said transparent element.

7. An apparatus as in claim 6 wherein said conductive members are cylindrical and in combination with said opening of said transparent member form an elongated object receiving region.

8. An apparatus as in claim 5 wherein a selected fluid fills any remaining space between at least the object and the transparent element.

9. An apparatus as in claim 5 wherein said heat conductive member is cylindrical.

10. An apparatus for analysing the optical properties of a transparent object, comprising a light source, an analyser cell which includes a body of solid transparent material having a cavity formed therein for receiving the object to be analysed, and arranged so as to allow a light beam from said light source to pass through the object, said body having an entrance surface through which the light beam enters said cell from and ambient medium and an exit surface through which the light beam leaves said cell, and analysing means for analysing the light beam after passage through the object wherein said cavity is of a substantially circular section in at least a first region through which the light beam passes in use, wherein at least one heat conductive member is provided in a second region within said cavity and wherein the member is cylindrical and defines a central opening for receiving the object and substantially fills said second region except for said central opening.

11. An apparatus as in claim 10, which includes a second, cylindrical, conductive member wherein said members are spaced apart with said body positioned therebetween.

* * * * *